US007618950B2

(12) United States Patent
Yamamoto et al.

(10) Patent No.: US 7,618,950 B2
(45) Date of Patent: Nov. 17, 2009

(54) METHOD FOR TREATMENT AND PREVENTION OF HERPES ZOSTER BY TOPICAL APPLICATION

(75) Inventors: Masaichi Yamamoto, Tokyo (JP); Haruhiko Machida, Fuchu (JP)

(73) Assignee: aRigen Pharmaceuticals, Inc., Tokyo (JP)

( * ) Notice: Subject to any disclaimer, the term of this patent is extended or adjusted under 35 U.S.C. 154(b) by 365 days.

(21) Appl. No.: 10/886,503

(22) Filed: Jul. 7, 2004

(65) Prior Publication Data

US 2006/0009401 A1   Jan. 12, 2006

(51) Int. Cl.
*A01N 43/04* (2006.01)
*A61K 31/70* (2006.01)

(52) U.S. Cl. .......................................... 514/50; 514/49
(58) Field of Classification Search .................. 514/49, 514/50

See application file for complete search history.

(56) References Cited

U.S. PATENT DOCUMENTS

| 4,386,076 A | | 5/1983 | Machida et al. |
| 5,034,382 A | * | 7/1991 | Osswald ....................... 514/46 |
| 6,337,324 B1 | * | 1/2002 | Harmenberg et al. ........ 514/171 |

FOREIGN PATENT DOCUMENTS

JP   56-087599   7/1981

OTHER PUBLICATIONS

Wikipedia, definition for "Herpes Zoster", last updated Sep. 5, 2006.*
Diasio et al., "Sorivudine and 5-FU; a clinically significant drug-drug interaction due to inhibition of dihydropyrimidine dehydrogenase", Br. J. Clin. Pharmacol., vol. 46, pp. 1-4, 1998.*

Katsushi Ijichi, et al.; "Topical treatment with BV-araU of immunosuppressed and immun ocompetent shaved mice cutaneously infected with herpes simples virus type 1"; Antiviral Research, 21 (1993), pp. 47-57; ©1993 Elsevier Science Publishers B.V.
"Lecture Summaries of the '99 Pharmaceutical Society of Japan, p. 213, 30C10-2". English-language summary attached, published Jul. 20, 1979.
Lieve Naesens et al., entitled "Recent Developments in Herpesvirus Therapy," Herpes, 2001, pgs. 12-16, 8:1.
Stephen E. Straus, M.D., entitled "Clinical and Biological Differences Between Recurrent Herpes Simplex Virus and Varicella-Zoster Virus Infections," JAMA, Dec. 22-29, 1989, pp. 3455-3458, vol. 262, No. 24.
Peter Wutzler, entitled "Antiviral Therapy of Herpes Simplex and Varicella-zoster Virus Infections," Intervirology 1997, pgs. 343-356, vol. 40.
Erik De Clercq, entitled "Antiviral Drugs in Current Clinical Use," Journal of Clinical Virology 30, 2004, pp. 115-133.

* cited by examiner

*Primary Examiner*—Traviss C McIntosh, III
(74) *Attorney, Agent, or Firm*—The Webb Law Firm

(57) ABSTRACT

A method for the treatment and prevention of herpes zoster using 5-[(E)-2-halogenovinyl] arabinofuranosyl uracil of the following general formula (1):

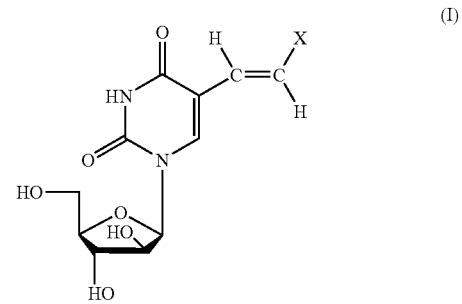

wherein X represents a halogen atom.

4 Claims, 2 Drawing Sheets

Changes in pain scores

Changes in vesicle score

METHOD FOR TREATMENT AND PREVENTION OF HERPES ZOSTER BY TOPICAL APPLICATION

TECHNICAL FIELD

The present invention relates to a method for the treatment and prevention of herpes zoster by the topical application.

BACKGROUND OF THE INVENTION

Herpes zoster virus is one of herpes virus group. Herpes viruses are DNA viruses with double-stranded DNA genomes, a regular icosahedron capsid, and an envelope derived from the nuclear membrane of the host cell. There are eight types of human herpes viruses including 1) herpes simplex virus type 1 (HSV-1), 2) herpes simplex virus type 2 (HSV-2), 3) varicella zoster virus (VZV), 4) Epstein-Barr virus (EBV), 5) cytomegalovirus (CMV), 6) human herpes virus type 6, 7) human herpes virus type 7 and 8) human herpes virus type 8. Herpesviridae viruses establish latent infections after initially infecting the human body. They are re-activated when the human host becomes immunocompromised to cause a diseased condition (recurrence). In other words, the primary infection is an exogenous infection from hosts or environments having viruses (horizontal infection or vertical infection). Recurrence is an intrinsic infection from within. The VZV lies in particular hidden in the ganglions. It is re-activated when the host becomes immunocompromised and produces rashes and herpes accompanying pains along ganglions (herpes zoster). Herpes diseases tend to increase according to aging, stress, and an increase in AIDS patients, becoming a major social issue.

There are no topical products specifically approved for the treatment of herpes zoster in the US. Commercially available products as anti-herpes virus agents are famciclovir, valacyclovir and acyclovir, which are intravenously or orally administered. The labeling for Famvir (famciclovir) states that the product was not studied in immunocompromised patients with herpes zoster and includes as a precaution the statement: "The efficacy of Famvir (famciclovir) has not been established in immunocompromised patients with herpes zoster." The labeling for Valtrex (valacyclovir) describes clinical trials conducted in immunocompetent (but not immunocompromised) adults with herpes zoster. However, the labeling of Valtrex includes the following warning; thrombocytopenic purpura/hemolytic uremic syndrome, in some cases resulting in death, has occurred in patients with advanced HIV disease and also in allogenic bone marrow transplant and renal transplant recipients participating in clinical trials. The labeling for Zovirax (acyclovir) tablets describes clinical trials conducted in immunocompetent (but not immunocompromised) adults with herpes zoster. Intravenous acyclovir is the only product currently indicated for treatment of herpes zoster in immunocompromised patients.

Japanese Patent Publication No. 48160/1982 (U.S. Pat. No. 4,386.076) discloses that 5-[(E)-2-halogenovinyl]-arabinofuranosyluracil possesses potent antiviral activity. Of these uracils, 1-β-D-arabinofuranosyl-5-[(E)-2-bromovinyl]uracil (nonproprietary name: sorivudine:BVAU) has an extremely potent antiviral activity against HSV-1, EBV and VZV. This sorivudine was sold under the trade name of "Usevir" as tablets in Japan in 1993. As it was developed as an oral agent, patients administered sorivudine and fluorouracil-based anticancer drugs at the same time died because of the adverse effect due to drug interaction, which was a major problem. Later studies clarified the mechanism of interaction. The mechanism is one in which bromovinyluracil (BVU) as a principal metabolite of sorivudine inhibits the metabolism of fluorouracil and the concentration of fluorouracil in blood rises abnormally, causing serious myelo-suppression such as leucopenia and thrombocytopenia as adverse effects of this anti-cancer drug.

When drugs are administered orally, large amounts are administered for the agents to reach the targeted area. When sorivudine is orally administered in large amounts, a large portion of this as is absorbed by the intestines is discharged in urine through the kidneys. In the intestines, another portion of this drug is metabolized into bromovinyluracil (BVU) by intestinal bacteria and re-absorbed. The re-absorbed BVU inhibits dihydropyrimidine dehydrogenase (DPD) as a metabolic enzyme for fluorouracil. Therefore, the metabolism of fluorouracil is suppressed and its toxicity increased.

Thus, sorivudine is not currently used because of serious drug interaction with fluorouracil based anticancer drugs.

On the other hand, it was reported that the application of sorivudine to the skin suppresses the skin symptoms caused by inoculation with HSV-1 in mice (Antiviral Research, 21, 47-57, 1993). However, it is not disclosed that the topical application of sorivudine is effective for the treatment or prevention of herpes zoster. In the past, animal experimental model for herpes zoster could not be constructed and therefore therapeutic efficacies for herpes zoster could not be demonstrated. Furthermore, 5-[(E)-2-halogenovinyl]-arabinofuranosyluracil including sorivudine is slightly soluble and therefore the topical preparation for practical use was difficult to make. Additionally, interaction of these compounds with fluorouracil-based agents has not been investigated when used as a topical preparation.

SUMMARY OF THE INVENTION

It is an object of the present invention to provide a method for the treatment or prevention of herpes zoster by the topical application.

It is an another object of the present invention to provide a method for treating or preventing herpes zoster effectively, safely and without displaying side-effects such as interaction with fluorouracil-based anticancer drugs.

The present inventors have investigated to use sorivudine and related compounds as topical preparations for herpes zoster, developed the stable preparations comprising them for topical use such as cream, ointments and gels and conducted a clinical trial.

The inventors have found that the topical application of sorivudine and related compounds can effectively inhibit the growth of varicella zoster virus (VZV), and avoid the interaction with fluorouracil-based agents, which was a serious problem when orally administered.

The present invention provides a method for the treatment or prevention of herpes zoster, comprising topically administering to a patient an effective amount of 5-[(E)-2-halogenovinyl]arabinofuranosyl uracil having the following general formula (I).

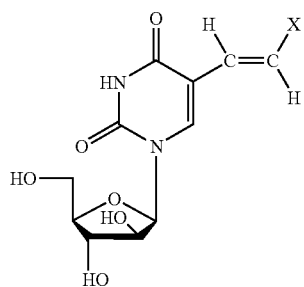

(I)

wherein, X represents a halogen atom.

In formula (I) above, X is preferably a chlorine or bromine atom.

The present invention also provides a pharmaceutical composition for the treatment or prevention of herpes zoster, comprising 5-[(E)-2-halogenovinyl]arabinofuranosyl uracil as an active ingredient and a pharmaceutically acceptable base for topical application.

DETAILED DESCRIPTION OF THE PREFERRED EMBODIMENTS

Figure 1:
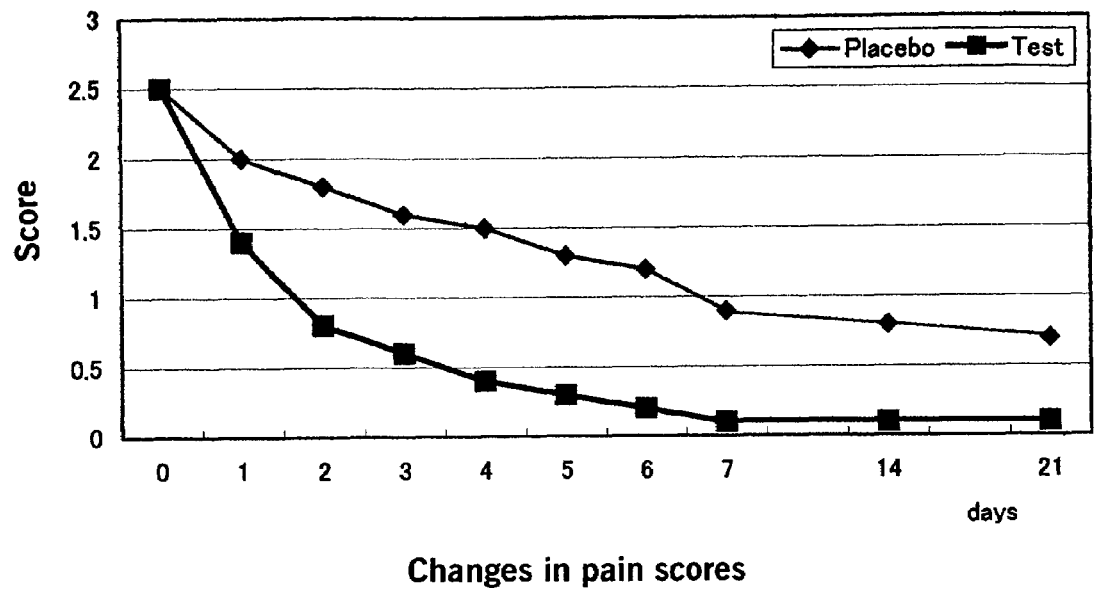
FIG. 1 is a graph of changes in pain score after treatment of Sorivudine 3% cream.

The present invention will be explained further in detail as follows.

5-[(E)-2-halogenovinyl]arabinofuranosyl uracil having the formula (I) used in the present method for the treatment or prevention of herpes zoster by the topical application is described in Japanese Patent Publication No. 48160/1982 (U.S. Pat. No. 4,386,076). This compound possesses selective inhibitory activity against VZV and markedly low inhibitory activity on the proliferation of cells not infected with the virus. This compound may be prepared by known methods, for example, the methods described in the Japanese Patent Publication above, or similar methods. For example, it may be synthesized by the reaction of 5-vinylarabinofuranosyluracil with a halogen. The synthesis of 5-vinylarabinofuranosyluracil used is, for example, described in Lecture Summaries of the Pharmaceutical Society of Japan, p. 213, 30C10-2.

In the general formula (I), X represents a halogen atom such as a chlorine, bromine, iodine, or fluorine atom.

1-β-D-Arabinofuranosyl-5-[(E)-2-bromovinyl]uracil (nonproprietary name: sorivudine), a compound in the event X is a bromine atom, and 1-β-D-arabinofuranosyl-5-[(E)-2-chrolovinyl]uracil (referred to as CVAU), a compound in the event X is a chlorine atom, are preferably used.

According to the present invention, the compound of formula (I) is administered topically to a patient with herpes zoster. The compound may be formulated into various forms along with appropriate bases as are pharmaceutically acceptable for a preparation for topical use. Bases that are commonly used in the manufacture of preparations for topical use can be used. However, bases with less irritation and pain upon application are selected for use with patients with abnormal skin of herpes zoster. Forms of preparation may be cream, ointment, gel, pap, plaster, patch, or the like. In formulating the compound of formula (I) with appropriate bases, one or more steps may be conducted by warming under reduced pressure.

When manufacturing ointments, creams, and gels, an oleaginous base or emulsion base may be used as a base. Ointments may be manufactured, for example, by warming, agitating, and mixing the active ingredient and optionally a base such as propylene glycol under reduced pressure into an oleaginous base. As an example of the manufacture of creams, the active ingredient as is warmed and dissolved into a base such as propylene glycol under reduced pressure is added to an emulsion base prepared in advance while warmed under reduced pressure. Gels may be manufactured by, for example, dissolving a gel base in water, adding a hydrophilic organic solvent to it, and adding it gradually to an active ingredient warmed and dissolved in a base such as dipropylene glycol.

Plasters, patches, and paps may be manufactured by flatting an ointment containing an active ingredient obtained according to the method above on a non-woven cloth or woven cloth as a support and cutting it into an appropriate size.

Oleaginous bases that can be used in this invention include fat, wax, hydrocarbon, fatty acid, alcohols, alkylglyceryl ether, esters, silicon oil, fluorine oil, polyhydric alcohol, etc.

A wide range of animal and plant fats and oils may be used. Plant oils include olive oil, safflower oil, persic oil, kukui nut oil, wheat germ oil, rice germ oil, evening primrose oil, haiorec sunflower oil, macadamia nut oil, meadowfoam seed oil. Animal fats include beef tallow, hardened oil, egg yolk oil, etc.

Waxes are constituted mainly with ester (wax ester) of higher fatty acids and higher alcohols. The carbon number to constitute the ester body is from C12 to C34. Animal waxes include lanolin, whale wax, beeswax, shellac wax, and liquid orange roughy oil. Plant waxes include carnauba wax, candelilla wax, and liquid jojoba oil.

Examples of hydrocarbon are chain hydrocarbons, and liquid paraffin, branched paraffin, solid paraffin and Vaseline that are mixtures of various hydrocarbons.

Fatty acids include natural and synthesized fatty acids. Examples include lauric acid, myristic acid, palmitic acid, stair acid, behenin acid, oleic acid, isostearic acid, 12-hydroxystearic acid, and undecylic acid.

Alcohols include, for example, higher alcohols of C8-C32 such as caprylyl alcohol, caprylic alcohol, lauryl alcohol, myristyl alcohol, cetyl alcohol, stearyl alcohol, oleyl alcohol, behenyl alcohol, ceryl alcohol, and lacceryl alcohol. Animal or plant sterols may be used.

Alkylglycerylether includes batyl alcohol, chimyl alcohol, selachyl alcohol, and isostearyl glycerylether.

Esters are compounds obtained from a dehydration reaction of fatty acids and alcohols. Esters of straight-chain fatty acids and lower alcohols include ethyl oleate, isopropyl myristate, and butyl stearate. Esters of straight-chain fatty acids and straight-chain higher alcohols include cetyl palmitate and myristyl myristate. Esters of straight-chain fatty acids and branched chain higher alcohols include octyl dodecyl myristate and octyldodecyl oleate. Esters of straight-chain fatty acids and polyhydric alcohols include medium-chain triglyceride. Esters of branched chain fatty acids and lower alcohols include isopropyl stearate and butyl isostearate. Esters of branched fatty acids and straight-chain higher alcohols include 2-ethylhexane cetyl and 2-ethylhexane stearyl. Esters of branched fatty acids and straight-chain higher alcohols or branched fatty acids and branched higher alcohols include isocetyl isostearate and octyldodecyl dimetyleoctanoic. Esters of hydroxycarboxylic acids and alcohols include myristyl lactate, trioctyldodecyl citrate, and diisostearyl malate.

Silicon oils include dimethyl silicon oil, methylphenyl silicon oil, cyclic dimethyl silicone oil, methylhydrogen silicon oil, and modified silicon oil. Fluoride oils include parfluoropolyether.

Polyhydric alcohols include ethylene glycol, diethylene glycol, triethylene glycol, poly ethylene glycol, polypropylene glycol, glycerin, diglycerin, polyglycerin, 3-metyl-1,3-buthane diol, and 1,3-buthyleneglycol.

Emulsion bases that can be used in this invention include O/W base, W/O base, and lotion base. O/W bases include components such as lanoline, stearyl alcohol, vaseline, silicon oil, liquid paraffin, and glycerylmonostearate emulsified and dispersed in a water phase with or without surface-active surfactants. W/O bases include vaseline, higher fatty acid alcohol, and liquid paraffin emulsified and dispersed by adding water in the presence of nonionic surface-active agents.

Plasters and patches may be manufactured of support medium such as nonwoven cloth, elastic bodies such as natural rubber, polyisobutylene, butyl rubber, polyvinylalkylether, polyacrylate, polyurethane, and polyamide, acrylic ester/acrylic acid copolymer, and adhesive compounds such as poly terpene resin, rosin, or their esters. Varied fillers, release agents, and softeners may be mixed.

Paps may be manufactured by using support medium such as nonwoven cloth, bases such as pectin, polyacrylic acid and its salts, polyvinyl alcohol, polyvinyl pyrrolidone/ vinyl acetate copolymer, polyethylene oxide, carboxymethyl cellulose, hydroxy propyl cellulose, methylcellulose, alginate, xanthan gum, tragacanth gum or methylvinyl ether, and maleic anhydride copolymer. Adhesives that can be used include synthetic high polymer such as carboxyvinyl polymer and natural high polymer such as gum Arabic. Surface-active surfactants that can be used include polysolivate 80 and sorbitan sesquoleate. pH adjusters that can be used include citric acid and tartaric acid. Curing agents that can be used include polyvalent metal compounds such as zinc oxide and aluminum hydroxide.

Varied antioxidant substances may be used to improve the stability of preparations. Specific examples include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate. Further, antiseptic agents such as paraoxy benzoic acid, methylparaben, ethylparaben, propylparaben, and aromatics may be added.

Furthermore, moisturizing agents may be mixed in order to prevent dryness of the skin of patients infected with herpes zoster virus. Moisturizing agents include polyhydric alcohols, saccharides, and biological polymers. Polyhydric alcohols include glycerin, propylene glycol, 1,3-buthyleneglycol, polyethylene glycol, sorbitol, isoprene glycol, and POB methyl glucoside. Saccharides include trehalose, pullulan, and maltose. Biological polymers include sodium hyaluronate, chondroitin sodium sulfate, collagen, and elastin in addition to amino acids, sodium lactate, pyrrolidone sodium carboxylate, and urea. As anti-inflammatory agents, aminocarboxylic acid, glycyrrhizin acid, β-glycyrrhizin acid, lysozyme chloride, and hydrocortisone may be used.

The compound of formula (I) when topically administered is remarkably effective in treating herpes zoster in humans without serious side effects, as demonstrated in the following examples. The topical application of this compound can avoid interaction with fluorouracil-based agents as had become a problem with orally administered sorivudine and has no skin toxicity. Therefore, the present invention provides a method for a safe and effective treatment or prevention of the herpes zoster.

The dose of the compound of formula (I) differs depending on age, clinical conditions, gender, and days after onset. The pharmaceutical composition containing this compound for topical use may be applied to the skin of a patient in adequate quantity. Preferably, a composition containing 0.1-10%, and preferably 0.5-5% of the compound may be applied on skin lesions once or several times a day.

The following examples are intended to illustrate but not to limit the invention.

EXAMPLES

Example 1

Preparation of Cream

Monostearate acid POE (5) glycer 500 g, methylpolysiloxane 300 g, Cetanol 150 g, paraffin 500 g, Vaseline 900 g, glycermonostearate 50 g, and BHT 5 g were added, warmed to 75° C., and agitated under reduced pressure to make an even solution. A solution in which purified water 5.56 L and propyleneglycol 300 g were mixed and dissolved was added to the solution above. The solution is warmed, agitated, and emulsified under reduced pressure. Solutions of sorivudine 500 g, 300 g, and 100 g dissolved with propylene glycol 1.5 kg, 1.7 kg, and 1.9 kg respectively while warmed under reduced pressure at 75° C. were added gradually. The solution was cooled down to room temperature while it was agitated. Creams of sorivudine 5% 3% , and 1% were obtained.

A solution of CVAU 300 g and propylene glycol 1.7 kg were dissolved into the emulsion prepared in advance in the manner above in place of sorivudine as a main ingredient under reduced pressure at 75° C. The solution was added gradually in the same manner above. Thus, 10 kg of CAVU 3% cream was obtained.

Example 2

Preparation of Ointment

White petrolatum 2 kg and liquid paraffin 6 kg were dissolved while agitating at 75° C. Sorivudine 300 g and propylene glycol 1.7 kg were dissolved into the solution under reduced pressure at 75° C. 10 kg of sorivudine 3% ointment was obtained.

Example 3

Preparation of Gel

Carboxyvinylpolymer 200 g and methylcellulose 20 g were evenly dissolved into purified water. Further, 4 kg of PEG1500, 25 g of titan dioxide, and 25 g of EDTA were added. 3.5 kg of dipropylene glycol and 500 g of POE oleyl alcohol ether were added to 300 g of Sorivudine and heated and dissolved at 50-55° C. 250 g of parabene, an antiseptic agent, was added. The solution was added gradually into a water phase prepared in advance while agitating. Finally, 10 ml of potassium hydrate solution is added and well agitated for neutralization. 10 kg of sorivudine 3% gel was obtained.

Example 4

Preparation of Pap 100 g of Sorivudine and 50 g of polysolivate 80 were agitated and mixed into 1 kg of propyleneglycol under reduced pressure to make an even solution. Separately, 1.5 kg of glycerin, 500 g of titanium dioxide, and 500 g of sodium polyacrylate were mixed. 6.15 kg of purified water and 200 g of citric acid were added to the solution and heated and dissolved under reduced pressure at 50-55° C. to make an even solution. The solution prepared in advance was added to this solution gradually. The solution is heated and dissolved under reduced pressure at 50-55° C. to obtain pH5 sorivudine containing ointment. Then, this ointment is flattened on a cloth. The surface of the ointment is covered with a storage film and cut into a specified size. Paps containing Sorivudine 1% were obtained (No. 7).

Example 5

Clinical Test

The study was conducted in the medical facilities. Included in the study were adult 10 patients with moderate or severe herpes zoster in whom onset of the disease occurred within 3 days before treatment. Five patients were allocated in test group and others were in placebo group. A sorivudine topical cream intended for topical application to the areas on the skin with localized herpes zoster involvement was prepared.

Patients received either topical cream containing 3% of sorivudine once or twice daily or placebo cream for 7 days and observation was made for 14 days after completion of the treatment.

Severity of skin lesion was assessed before the start of the study. In general, the following parameters were evaluated daily during the therapeutic period:

Severity of skin lesion and pain; The severity of preblister erythema, vesicles, pustules, erosion/ulcers, eschar, rash and pain was evaluated according to the following 5 categories as follows; "very severe", "severe", "moderate", "mild" and "absent". The date of onset and disappearance were also recorded.

Viral shedding determination was conducted with vesicle fluid before treatment and during the therapeutic period. Collection of blister fluid was continued through the observation period if vesicles and/or pustules were present. Viruses were co-cultured for 21 days in a $CO_2$-incubator at 37° C. on confluent monolayers of fibroblasts derived from human fetal lungs. The presence or absence of VZV plaques (CPE) was determined.

Information of adverse events was recorded during the study if the investigator to be related to study medication.

Results

Efficacy on Pain

Changes in pain scores are shown in FIG. 1. Improvement was significant compared to the placebo group on the first day of treatment of sorivudine cream. The results showed pain relief by the treatment of topical application is very rapid.

Efficacy on Skin Symptoms

Figure 2:
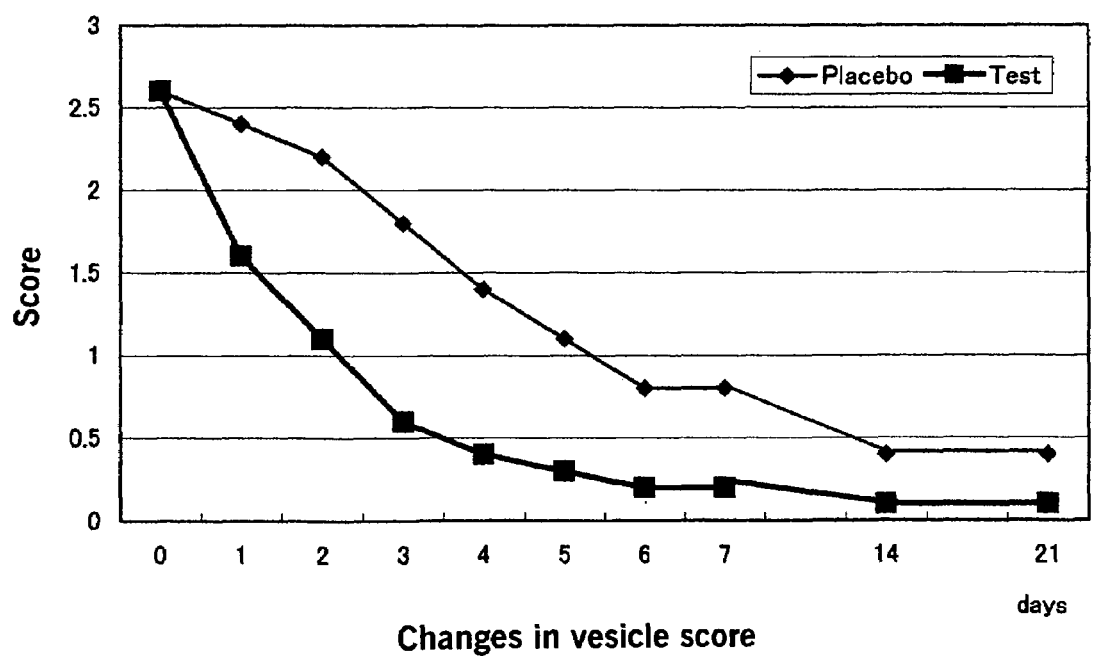
FIG. 2 shows the changes in vesicle score after treatment of Sorivudine 3% cream.

Improvement of skin symptom was significant compared to the placebo group. Topical treatment of sorivudine cream is very efficient for herpes zoster patients (FIG. 2).

Eradication of Viruses

Figure 3:
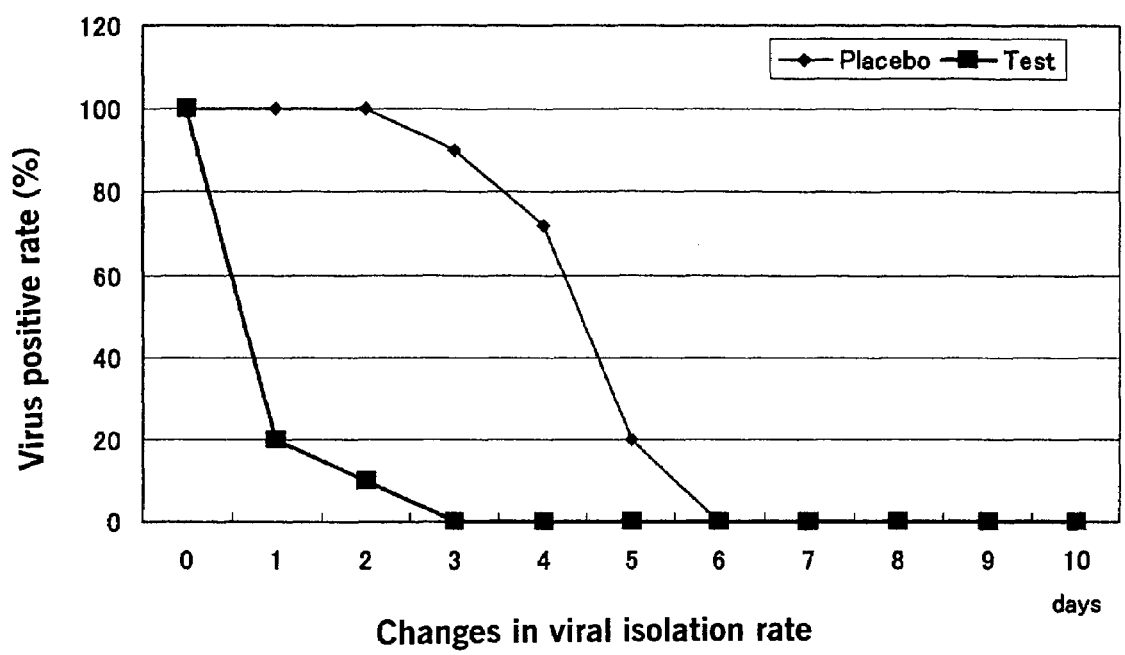
FIG. 3 is a graph of changes in viral isolation rate after treatment of Sorivudine 3% cream.

As shown in FIG. 3, days needed for virus eradication was observed only about two days after treatment of sorivudine topical cream. In other hand, eradication of virus took 5 to 6 days after the initiation of the treatment in placebo group.

Safety

There were no remarkable adverse events during the test period in both groups.

Example 6

Study of Interaction With 5-FU

Interactions with 5-FU, a fluorouracil-based anticancer drug, were studies using sorivudine (BVAU) 3% cream and CVAU 3% cream. Female Wister rats were raised for one week, and hair from the blade bone to the waist was shaved under anesthesia. The preparations for topical use were applied two times a day for one week. The expression "p.o." appearing in the table means oral administration.

The obtained results are shown in Table 1 below.

In Group 4 as a positive control, sorivudine was orally administered with 5-FU. This group expressed a side effect of significant weight loss and myelo-suppression due to the interaction. However, in Group 5 and Group 6, there was no interaction observed in the combination use of the preparations for topical use of this invention (sorivudine or CVAU for topical use) and 5-FU (Table 1).

This results indicate that the topical application of the compound of formula (I) can avoid the interaction with a fluorouracil-based anticancer drug even if used with this anticancer drug.

TABLE 1

| | Group | n | Body weight (pre./7 d) | Feed intake (pre./7 d) | Erythrocyte count ($10^4$/mm$^3$) | leukocyte count ($10^2$/mm$^3$) |
|---|---|---|---|---|---|---|
| Group 1 | untreated | 5 | 125/145 | 15/17 | 645 | 46.9 |
| Group 2 | BVAU (30 mg/kg, p.o.) | 5 | 124/143 | 15/16 | 653 | 45.6 |
| Group 3 | 5-FU (60 mg/kg, p.o.) | 5 | 125/146 | 15/15 | 648 | 47.8 |
| | Groups with concomitant dosing of agents | | | | | |
| Group 4 | BVAU(30 mg/kg/p.o.) + 5-FU(60 mg/kg, p.o.) | 5 | 125/88 | 16/3 | 892 | 5.8 |
| Group 5 | BVAU cream (3%)* + 5-FU(60 mg/kg, p.o.) | 5 | 125/147 | 15/15 | 651 | 45.9 |

TABLE 1-continued

| Group | | n | Body weight (pre./7 d) | Feed intake (pre./7 d) | Erythrocyte count ($10^4$/mm$^3$) | leukocyte count ($10^2$/mm$^3$) |
|---|---|---|---|---|---|---|
| Group 6 | CVAU cream (3%)* + 5-FU(60 mg/kg, p.o.) | 5 | 123/145 | 16/17 | 645 | 44.7 |

*Preparations for topical use were administered two times a day for one week.
**(Pre/7 d): before test/seven days after start of administration Erythrocyte count and leukocyte count are values measured seven days after the start of administration.

What is claimed is:

1. A method for the treatment and prevention of herpes zoster, comprising topically administering to a patient in need thereof an effective amount of 5-[(E)-2-halogenovinyl] arabinofuranosyl uracil having the following general formula (I):

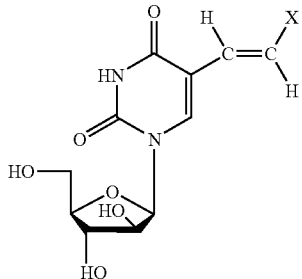
(I)

wherein X represents a halogen atom, thereby eradicating varicella zoster virus at a site of topical application.

2. A method according to claim 1, wherein X in the general formula (I) is a bromine atom or chlorine atom.

3. The method according to claim 1, comprising topically administering to a patient in need thereof an effective amount of sorivudine.

4. The method according to claim 1, comprising topically administering to a patient in need thereof an effective amount of 5-[(E)-2-halogenovinyl] arabinofuranosyl uracil over a period of two to seven days.

* * * * *

UNITED STATES PATENT AND TRADEMARK OFFICE
CERTIFICATE OF CORRECTION

PATENT NO. : 7,618,950 B2  Page 1 of 1
APPLICATION NO. : 10/886503
DATED : November 17, 2009
INVENTOR(S) : Yamamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 743 days.

Signed and Sealed this

Twenty-sixth Day of October, 2010

David J. Kappos
*Director of the United States Patent and Trademark Office*